(12) United States Patent
Chon et al.

(10) Patent No.: US 10,660,624 B2
(45) Date of Patent: May 26, 2020

(54) SURGICAL HANDPIECE HAVING DIRECTION-SHIFTING FUNCTION

(71) Applicant: Sciencemedic Co., Ltd., Anyang-si, Gyeonggi-do (KR)

(72) Inventors: Ki Jung Chon, Anyang-si (KR); Heon Hang Lim, Anyang-si (KR)

(73) Assignee: SCIENCEMEDIC CO., LTD., Anyang-si, Gyeonggi-do (KR)

( * ) Notice: Subject to any disclaimer, the term of this patent is extended or adjusted under 35 U.S.C. 154(b) by 129 days.

(21) Appl. No.: 15/565,143

(22) PCT Filed: Mar. 25, 2016

(86) PCT No.: PCT/KR2016/003045
§ 371 (c)(1),
(2) Date: Oct. 6, 2017

(87) PCT Pub. No.: WO2016/163671
PCT Pub. Date: Oct. 13, 2016

(65) Prior Publication Data
US 2018/0078246 A1    Mar. 22, 2018

(30) Foreign Application Priority Data
Apr. 8, 2015  (KR) .......................... 10-2015-0049646

(51) Int. Cl.
*A61B 17/00*    (2006.01)
*B25F 5/00*    (2006.01)
(Continued)

(52) U.S. Cl.
CPC .......... *A61B 17/00* (2013.01); *A61B 17/1622* (2013.01); *A61B 17/1626* (2013.01);
(Continued)

(58) Field of Classification Search
CPC . A61B 17/00; A61B 17/1622; A61B 17/1626; A61B 17/1628; A61B 17/1624;
(Continued)

(56) References Cited

U.S. PATENT DOCUMENTS 4,204,580 A  *  5/1980  Nalley ................... B25D 16/00
                                                      173/170
5,277,527 A  *  1/1994  Yokota .................. B23B 45/008
                                                      192/150
(Continued)

FOREIGN PATENT DOCUMENTS

JP    2007-030093 A    2/2007
JP    2008-537901 A    10/2008
(Continued)

*Primary Examiner* — Alex M Valvis
*Assistant Examiner* — Scott A Howell
(74) *Attorney, Agent, or Firm* — Rabin & Berdo, P.C.

(57) ABSTRACT

The present invention relates to a surgical handpiece and more specifically, to a surgical handpiece having a direction-shifting function, which has a switch capable of easily shifting the direction when the direction of the handpiece needs to be shifted during surgery.

The surgical handpiece having a direction-shifting function includes: a handgun-shaped housing having a grip and a motor housing integrally formed at the upper part of the grip; a trigger provided at the front surface of the grip to control a rotational speed of the handpiece; a motor having a driving shaft provided in the motor housing; a direction-shifting switch unit including a direction-shifting switch formed to protrude from the side surface of the grip, a link mechanism provided inside the grip and moving by being linked to the direction-shifting switch, and a sensor sensing the movement of the link mechanism; and a control unit provided inside the grip, analyzing a signal transmitted from the
(Continued)

sensor to shift the rotational direction of the motor, and controlling the speed of the motor by the trigger.

3 Claims, 6 Drawing Sheets

(51) Int. Cl.
 *B25F 5/02* (2006.01)
 *A61B 17/16* (2006.01)
(52) U.S. Cl.
 CPC .......... *A61B 17/1628* (2013.01); *B25F 5/008* (2013.01); *B25F 5/02* (2013.01); *A61B 17/1624* (2013.01); *A61B 2017/0042* (2013.01); *A61B 2017/00398* (2013.01); *A61B 2017/00544* (2013.01); *A61B 2017/00734* (2013.01)
(58) Field of Classification Search
 CPC .. A61B 2017/1624; A61B 2017/00398; A61B 2017/0042; A61B 2017/00544; A61B 2017/00734; B25F 5/008; B25F 5/02
 USPC .............................................. 173/217; 227/15
 See application file for complete search history.

(56) References Cited

U.S. PATENT DOCUMENTS

| | | | |
|---|---|---|---|
| 6,059,806 A * | 5/2000 | Hoegerle | A61B 17/1628 606/180 |
| 7,185,713 B2 * | 3/2007 | Lee | B23B 45/008 173/176 |
| 7,638,958 B2 | 12/2009 | Philipp et al. | |
| 7,942,211 B2 * | 5/2011 | Scrimshaw | B23B 31/123 173/176 |
| 8,029,510 B2 * | 10/2011 | Hoegerle | A61B 17/1613 335/219 |
| 8,403,076 B2 * | 3/2013 | Iwakami | B25D 17/043 173/162.1 |
| 8,410,645 B2 * | 4/2013 | Lau | B25F 5/008 173/217 |
| 8,657,482 B2 | 2/2014 | Malackowski et al. | |
| 9,457,462 B2 * | 10/2016 | Mergener | B25F 5/001 |
| 9,737,984 B2 * | 8/2017 | Yamamoto | B25F 5/001 |
| 9,744,658 B2 * | 8/2017 | Simeone | B23B 45/02 |
| 9,878,435 B2 * | 1/2018 | Ito | B25F 5/008 |
| 2008/0150375 A1 * | 6/2008 | Shima | B25F 5/008 310/50 |
| 2014/0014385 A1 * | 1/2014 | Kosugi | B25F 5/02 173/217 |
| 2015/0041164 A1 * | 2/2015 | Sergyeyenko | B25B 21/008 173/1 |
| 2015/0333664 A1 * | 11/2015 | Bantle | H02P 1/22 173/217 |
| 2016/0046011 A1 * | 2/2016 | Ogle | B24B 23/02 173/1 |
| 2016/0199972 A1 * | 7/2016 | Kishima | B23B 45/02 173/46 |

FOREIGN PATENT DOCUMENTS

| | | |
|---|---|---|
| KR | 10-0549101 B1 | 1/2006 |
| KR | 10-1440740 B1 | 9/2014 |
| KR | 10-2014-0133934 A | 11/2014 |

* cited by examiner

SURGICAL HANDPIECE HAVING DIRECTION-SHIFTING FUNCTION

TECHNICAL FIELD

The present invention relates to a surgical handpiece and more specifically, to a surgical handpiece having a direction-shifting function, which has a switch capable of easily shifting the direction when the direction of the handpiece needs to be shifted during surgery.

BACKGROUND ART

Generally, an appearance of a surgical handpiece has a handgun-shaped structure, and a pneumatic motor is generally used as a driving power source of the handpiece. The handpiece has a structure in which the rotational force of the pneumatic motor is applied to a cutting tool (drill) through a gear assembly. Also, it is necessary to rotate a bur or drill mounted on the handpiece in a reverse direction by shifting the rotational direction of the pneumatic motor during surgery.

When describing techniques capable of shifting the rotational direction of the pneumatic motor, Korean Patent Publication No. 10-2014-0133934 relates to a surgical system including an electric rotary handpiece. The surgical system includes a surgical handpiece having a housing having a grip and a driving shaft rotatably held by the housing; a trigger assembly configured to generate a signal representing a user's desired speed, in which the trigger includes a trigger held by the grip; and a mode selection assembly configured to generate a signal representing a user's desired rotational direction, which includes a collar held by a housing adjacent to the grip, in which the handpiece is configured so that the index finger of the user's palm may selectively interact with the trigger and the collar when the grip is gripped in the palm of a user's hand. The technique has a mode selection assembly for changing the rotational direction, but there is a problem in that the structure is complicated and it is difficult to manufacture.

Further, Korean Patent Registration No. 10-0549101 relates to a surgical punching drill including: a drill body having a handgun-shaped structure and a drill chuck driven by a pneumatic motor, in which the drill body has a valve mounting portion vertically formed inside a grip, a motor mounting portion formed at the inner rear end of a head portion, and a gear mounting portion formed at the inner front end of the head portion of the drill body, the motor mounting portion is mounted with a pneumatic motor and the valve mounting portion is mounted with a valve assembly for providing a gas flow path through which gas input from a gas source is transferred to the pneumatic motor and controlling the gas flow on the gas flow path, a trigger member for controlling the gas flow path by operating the valve assembly is provided at an upper end of the valve assembly, the gear mounting portion is mounted with a gear assembly for rotating a drill chuck by receiving a rotational force through a shaft coupled to the pneumatic motor, only the valve assembly that does not cause heat generation is mounted on the grip of the drill body, and the pneumatic motor is mounted on the head portion of the drill body, thereby preventing the grip from being heated. The technique has a simple structure, but does not provide a technique for shifting the direction of the drill.

DISCLOSURE

Technical Problem

The present invention has been made in an effort to provide a surgical handpiece having a simple structure and easily shifting a direction.

Further, the present invention has been made in an effort to provide a surgical handpiece having cooling fins capable of cooling heat generated from a motor.

Technical Solution

An exemplary embodiment of the present invention provides a surgical handpiece having a direction-shifting function including: a handgun-shaped housing having a grip and a motor housing integrally formed at the upper part of the grip; a trigger provided at the front surface of the grip to control a rotational speed of the handpiece; a motor having a driving shaft provided in the motor housing; a direction-shifting switch unit including a direction-shifting switch formed to protrude from the side surface of the grip, a link mechanism provided inside the grip and moving by being linked to the direction-shifting switch, and a sensor sensing the movement of the link mechanism; and a control unit provided inside the grip, analyzing a signal transmitted from the sensor to shift the rotational direction of the motor, and controlling the speed of the motor by the trigger.

The motor may have a heat dissipation structure formed outside the cover. The heat dissipation structure may have a plurality of fins formed on the outer periphery surface in a longitudinal direction or a plurality of protrusion fins having a circular or polygonal section formed on the outer periphery surface of the cover.

The direction-shifting switch unit may include a direction-shifting switch protruding from a hole formed at the side of the grip; a link mechanism provided inside the grip and moving by being linked to the direction-shifting switch; a sensor mounted on a printed circuit board provided at the rear side of the link mechanism to sense the movement of the link mechanism; and a display unit displaying a forward/reverse direction according to an operation of the direction-shifting switch and provided on the bottom of the motor housing.

The control unit may be formed on the printed circuit board, analyzes a transmission signal of the sensor according to the operation of the direction-shifting switch to shift the rotational direction of the motor, and controls the speed of the motor according to the operation of the trigger.

The direction-shifting switch may include a switch housing fixed to the inside of the grip, an elastic member provided inside the housing, and a switch body moving to an original position by elasticity of the elastic member and having a bar extended downward, the link mechanism may have a bar insertion groove formed to be elongated downward and to which the bar of the switch body is inserted at the upper part, and a rotational shaft groove formed at the lower part of the bar insertion groove, and a rotational shaft may be mounted on the rotational shaft groove, the bar may push the link mechanism according to the movement of the switch body, and the link mechanism may rotate at a predetermined angle based on the rotational shaft by the pushing force of the bar.

Advantageous Effects

According to the present invention, since the structure is simple and the direction is easily shifted, it is advantageous that the user can easily use the surgical handpiece.

Further, since heatable cooling fins are provided on the outer periphery surface of the housing of the motor, it is advantageous that the cooling fins can cool heat generated by the motor.

MODES OF THE INVENTION

An exemplary embodiment of the present invention provides a surgical handpiece having a direction-shifting function including: a handgun-shaped housing having a grip and a motor housing integrally formed at the upper part of the grip; a trigger provided at the front surface of the grip to control a rotational speed of the handpiece; a motor having a driving shaft provided in the motor housing; a direction-shifting switch unit including a direction-shifting switch formed to protrude from the side surface of the grip, a link mechanism provided inside the grip and moving by being linked to the direction-shifting switch, and a sensor sensing the movement of the link mechanism; and a control unit provided inside the grip, analyzing a signal transmitted from the sensor to shift the rotational direction of the motor, and controlling the speed of the motor by the trigger.

Hereinafter, a surgical handpiece having a direction-shifting function of the present invention will be described with reference to the accompanying drawings.

Figure 1:
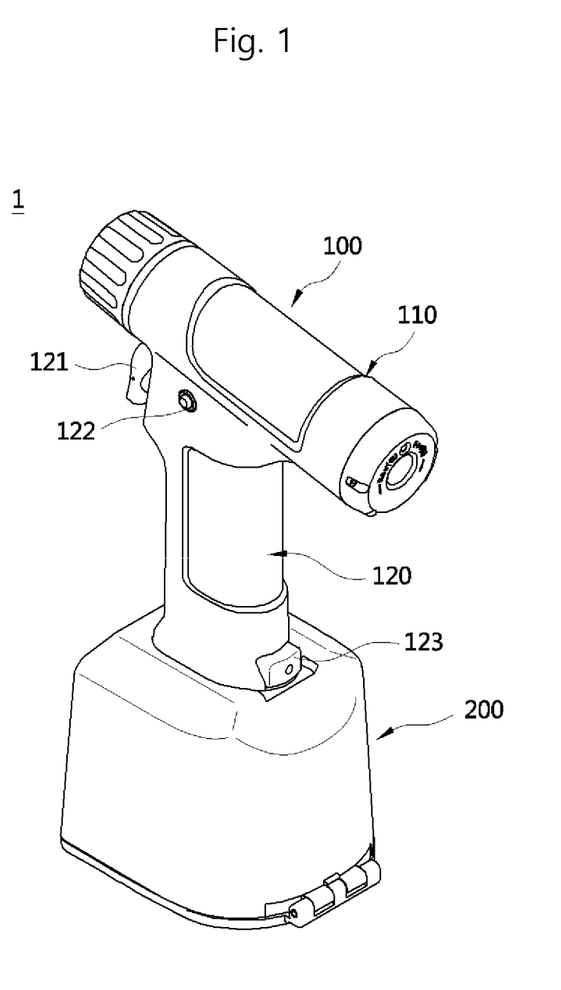
FIG. 1 is a perspective view of a surgical handpiece according to a preferred exemplary embodiment of the present invention.
Figure 2:
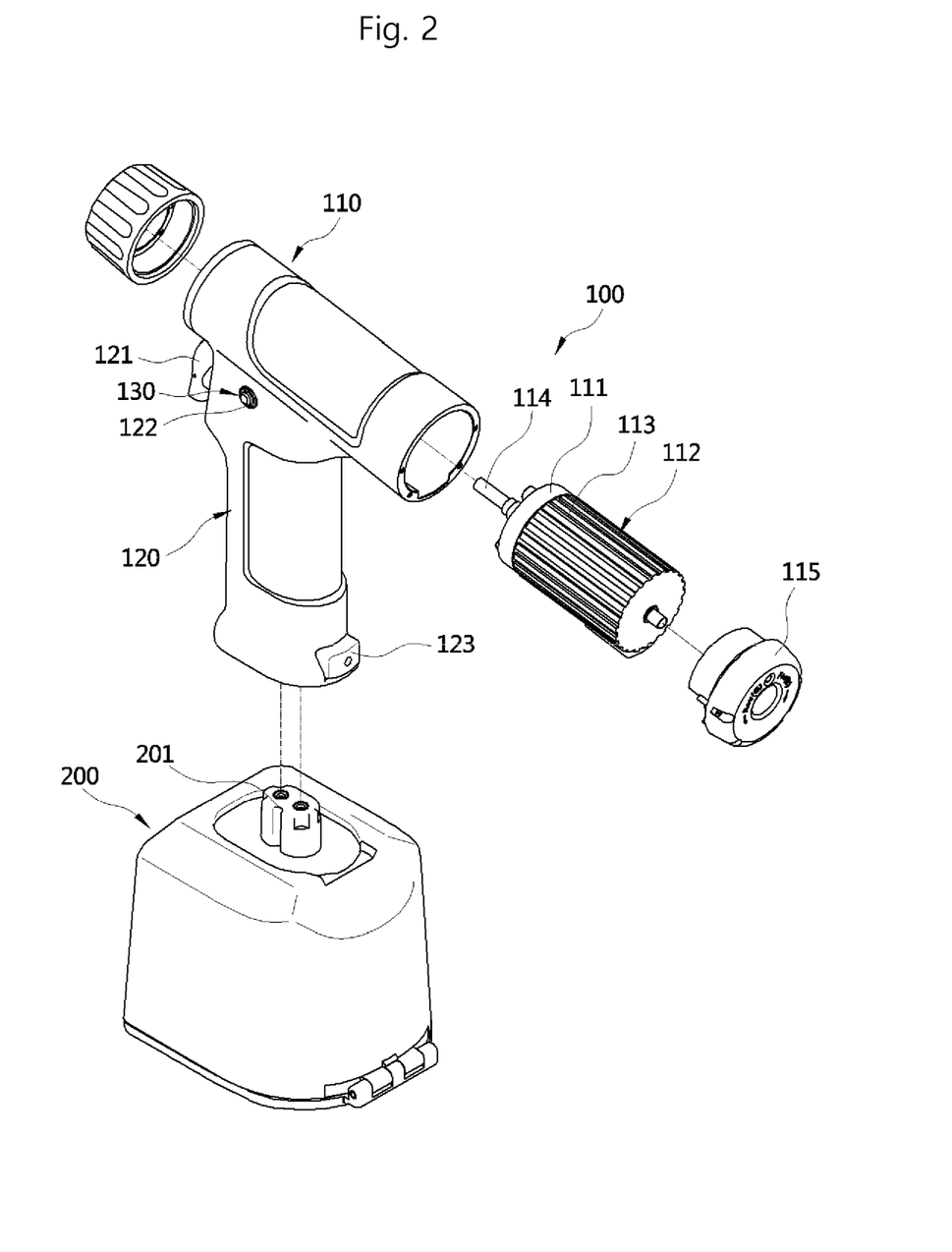
FIG. 2 is an exploded perspective view of the surgical handpiece according to the preferred exemplary embodiment of the present invention.
Figure 3:
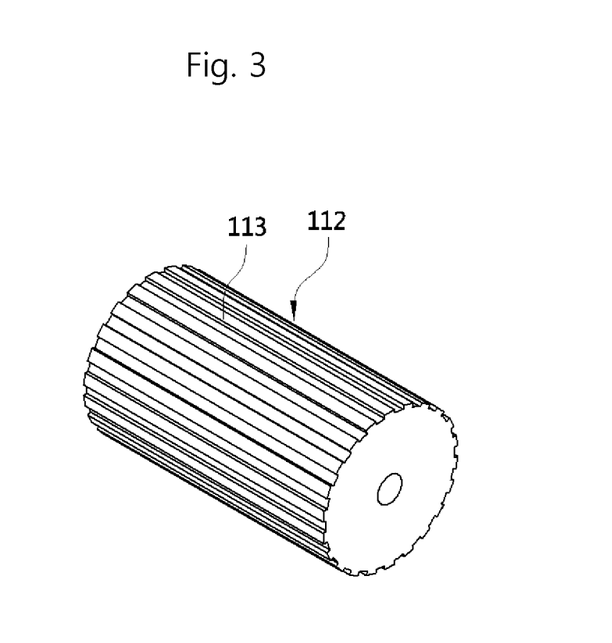
FIGS. 3 to 5 are perspective views for examples of a heat dissipation structure of a motor.
Figure 4:
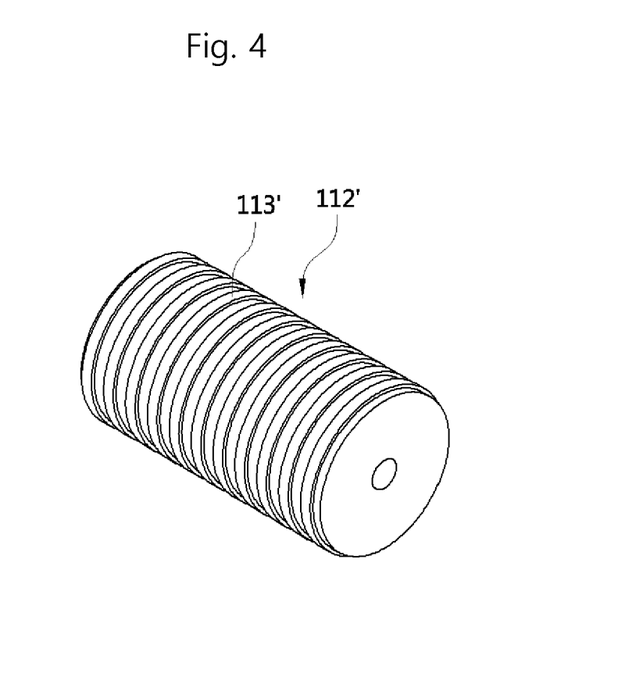
Figure 5:
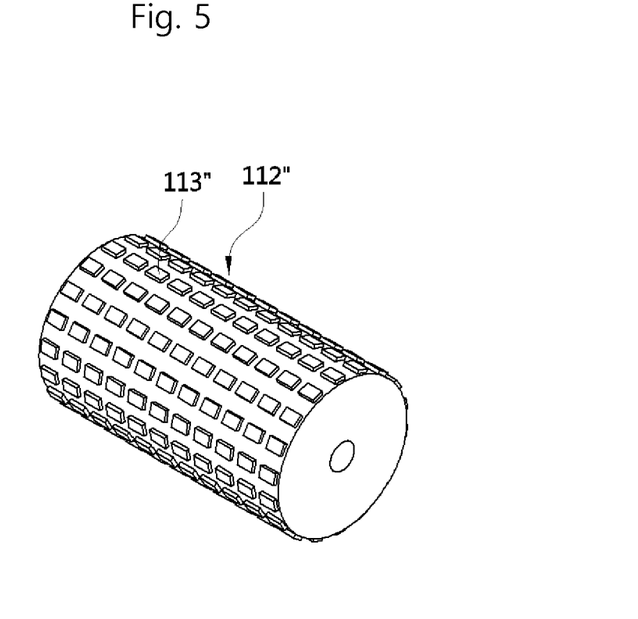
Figure 6:
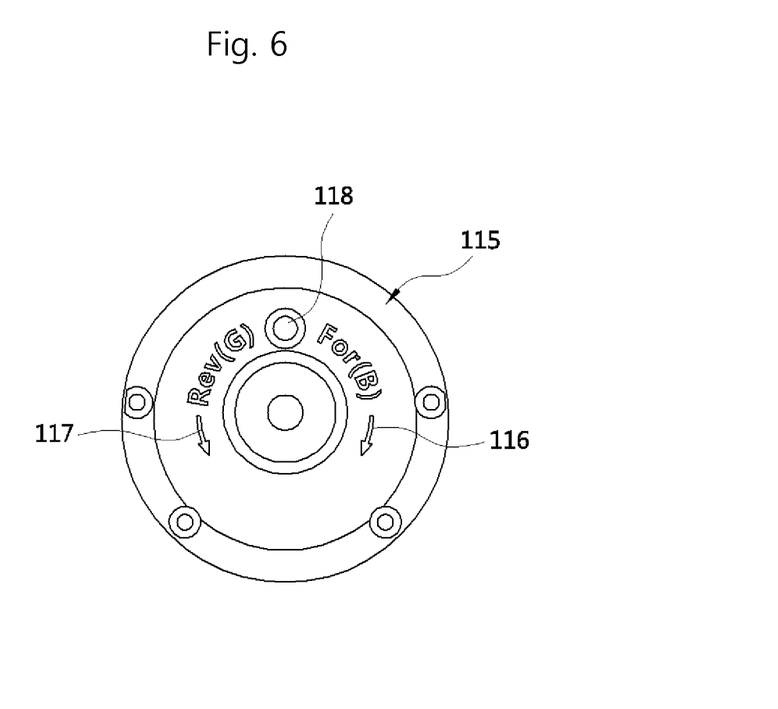
FIG. 6 is a perspective view of a display unit at a bottom side of the surgical handpiece according to the preferred exemplary embodiment of the present invention.
Figure 7:
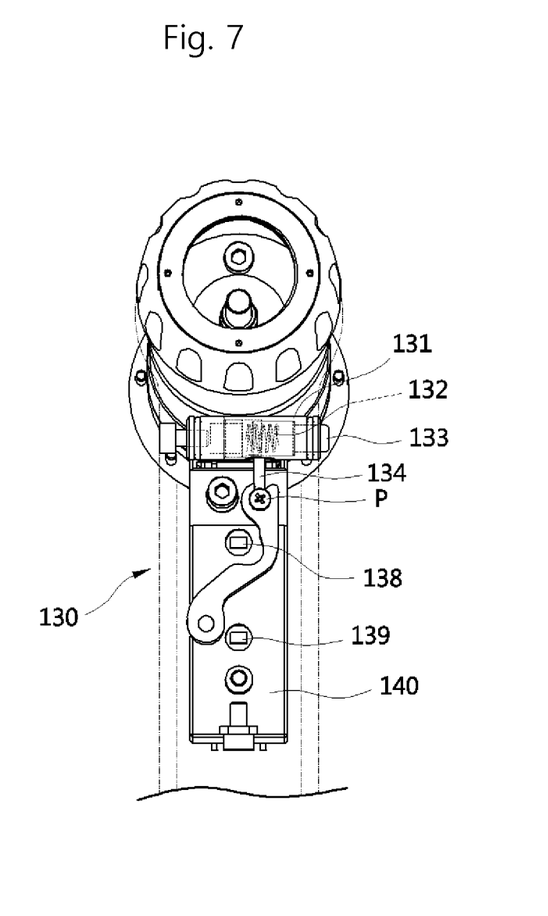
FIG. 7 is a front view of a direction-shifting switch unit of the surgical handpiece according to the preferred exemplary embodiment of the present invention.
Figure 8:
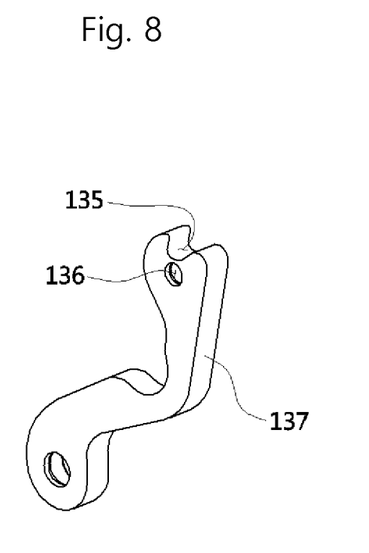
FIG. 8 is a front view of a link mechanism in FIG. 7.

FIG. 1 is a perspective view of a surgical handpiece according to a preferred exemplary embodiment of the present invention, FIG. 2 is an exploded perspective view of the surgical handpiece according to the preferred exemplary embodiment of the present invention, FIGS. 3 to 5 are perspective views for examples of a heat dissipation structure of a motor, FIG. 6 is a perspective view of a display unit at a bottom side of the surgical handpiece according to the preferred exemplary embodiment of the present invention, FIG. 7 is a front view of a direction-shifting switch unit of the surgical handpiece according to the preferred exemplary embodiment of the present invention, and FIG. 8 is a front view of a link mechanism in FIG. 7.

FIG. 1 is a perspective view of a surgical handpiece according to a preferred exemplary embodiment of the present invention. As illustrated in FIG. 1, a handpiece 1 of the present invention includes a housing 100 having a motor housing 110 and a grip 120, and a battery unit 200 provided at the lower part of the grip 120 to drive a motor. The battery unit 200 is coupled and provided to a joint installed at the lower part of the grip, and may be removed by pressing a detaching switch 123.

FIG. 2 is an exploded perspective view of the handpiece 1. As illustrated in FIG. 2, the motor 111 is provided in the motor housing 110. The motor 111 has a driving shaft 114 and cooling fins 113 for cooling heat according to the driving of the motor is formed on the outer periphery surface of the cover 112. A display unit 115 displaying a rotational direction of the motor is provided on the rear side of the motor and the battery unit 200 is coupled to the housing 100 by a joint 201 at the lower end of the grip 120. The attachment and the detachment of the battery unit 200 is performed by the detaching switch 123 and a fixing device (not illustrated) is released by pressing the detaching switch 123 to remove the battery unit 200. A trigger 121 is provided at the front side of the grip 120 to control the speed of the motor 111 provided in the handpiece. A mounting hole 122 in which the direction-shifting switch is mounted is provide at the side of the grip 120.

FIGS. 3 to 5 are views for a heat dissipation structure of the motor of the present invention. As illustrated in FIGS. 3 to 5, the heat dissipation structure of the motor is formed on the cover 112 and may be configured by fins 113 elongated in a longitudinal direction, fins 113' formed in circumferential ring shapes, or fins 113" protruding in polygonal cross sections. Accordingly, the heat dissipation structure may rapidly cool heat generated when the motor operates inside the handpiece 1, thereby enhancing durability of the handpiece 1 and solving problems such as damage on the skin by heat generated on the surface.

FIG. 6 is a view for the display unit 115. The display unit 115 is provided on the bottom side of the motor housing 110 to display forward rotation or reverse rotation of the motor and includes a forward display unit 116, a reverse display unit 117, and a direction indicator 118. The indicator 118 is configured by an LED or the like, and indicates blue B in the forward direction and green G in the reverse direction. Accordingly, the user can easily recognize the rotational direction of the motor according to the color of the indicator.

FIGS. 7 and 8 are views for the direction-shifting switch unit 130. As illustrated in FIGS. 7 and 8, the direction-shifting switch unit 130 includes a switch housing 131 fixed to the grip 120, a switch body 133 provided inside the switch housing 131 to move forward and backward, a spring 132 for returning to an original position when pressure is not applied to the switch body 133, a rod-shaped bar 134 extending downward from the lower end of the switch body 133, and a linker mechanism 137 having a bar insertion groove 135 to which the bar 134 is inserted and a rotational shaft groove 136. In the linker mechanism 137, when the pressure is applied to the switch body 133 by a rotational shaft P, the bar 134 is inserted to the bar insertion groove 135 to be formed in the linker mechanism 137 and pushes the front of the bar insertion groove 135, and as the bar insertion groove 135 is pushed, the linker mechanism 137 rotates at a predetermined angle based on the rotational shaft P.

A printed circuit board 140 mounted with the sensor 139 is provided at the rear side of the linker mechanism 137. The printed circuit board 140 has a trigger sensor 138 for sensing the movement of the trigger 121 and a control unit for controlling the speed of the motor or shifting the rotational direction of the motor according to a signal of the sensor.

An operation process of the surgical handpiece having the direction-shifting function according to the present invention will be described. When the user presses the trigger 121, a signal is transmitted to a controller by the trigger sensor 138 which senses the operation of the trigger 121, and the control unit which receives the signal from the trigger sensor 138 rotates the motor 111. In addition, the control unit controls the rotation speed of the motor according to the operation of the trigger 121. Next, the direction-shifting switch unit 130 determines the rotational direction of the motor. First, the motor 111 is fit to rotate in the forward direction. Accordingly, the color of the LED 118 displayed on the display unit 115 shines blue. When the user intends to shift the direction during surgery, the user presses the switch body 133 of the direction-shifting switch unit 130, the linker mechanism 137 rotates at a predetermined angle based on the rotational shaft P according to the movement of the switch body 133, and the movement is sensed by the linker mechanism sensor 139 and then the signal is transmitted to the control unit. The control unit receiving the signal from the linker mechanism sensor 139 shifts the direction in the reverse direction and simultaneously changes the LED 118 of the display unit 115 to green. Accordingly, the user may distinguish the current rotational direction of the motor by the color of the LED 118. When the user presses the switch body 133 again, the motor rotates in the forward direction and the color of the LED 118 is changed to blue.

INDUSTRIAL AVAILABILITY

The present invention relates to a surgical handpiece, and more particularly, to a surgical handpiece having a direction-shifting function, which has a switch capable of easily shifting the direction when the direction of the handpiece needs to be shifted during surgery and has high industrial availability.

The invention claimed is:

1. A surgical handpiece having a direction-shifting function, comprising:
   a handgun-shaped housing having a grip and a motor housing integrally formed at the upper part of the grip;
   a trigger provided at the front surface of the grip to control a rotational speed of the handpiece;
   a motor having a driving shaft provided in the motor housing;
   a direction-shifting switch unit including a direction-shifting switch protruding from a hole formed at the side of the grip, a link mechanism provided inside the grip and moving by being linked to the direction-shifting switch, a sensor mounted on a printed circuit board provided at the rear side of the link mechanism to sense the movement of the link mechanism, and a display unit displaying a forward/reverse direction according to an operation of the direction-shifting switch and provided on the rear of the motor housing; and
   a control unit provided inside the grip, analyzing a signal transmitted from the sensor to shift the rotational direction of the motor, and controlling the speed of the motor by the trigger,
   wherein the control unit is formed on the printed circuit board, analyzes a transmission signal of the sensor according to the operation of the direction-shifting switch to shift the rotational direction of the motor, and controls the speed of the motor according to the operation of the trigger,
   wherein the direction-shifting switch includes a switch housing fixed to the inside of the grip, an elastic member provided inside the housing, and a switch body moving to an original position by elasticity of the elastic member and having a bar extended downward,
   wherein the link mechanism has a bar insertion groove formed to be elongated downward and to which the bar of the switch body is inserted at the upper part, and a rotational shaft groove formed at the lower part of the bar insertion groove, and
   wherein a rotational shaft is mounted on the rotational shaft groove, the bar pushes the link mechanism according to the movement of the switch body, and the link mechanism rotates at a predetermined angle based on the rotational shaft by the pushing force of the bar.

2. The surgical handpiece of claim 1, wherein the motor has a heat dissipation structure formed outside the cover.

3. The surgical handpiece of claim 2, wherein the heat dissipation structure has a plurality of fins formed on the outer periphery surface in a longitudinal direction or a plurality of protrusion fins having a circular or polygonal section formed on the outer periphery surface of the cover.

* * * * *